United States Patent
D'Antonio et al.

(10) Patent No.: US 9,695,458 B2
(45) Date of Patent: Jul. 4, 2017

(54) SAMPLE DISH AND COMPRESSED GAS MICROBIAL TEST UNIT

(71) Applicant: Parker-Hannifin Corporation, Cleveland, OH (US)

(72) Inventors: John D'Antonio, Kittery, ME (US); H. Lee Scott, York, ME (US)

(73) Assignee: Parker-Hannifin Corporation, Cleveland, OH (US)

( * ) Notice: Subject to any disclaimer, the term of this patent is extended or adjusted under 35 U.S.C. 154(b) by 318 days.

(21) Appl. No.: 14/462,686

(22) Filed: Aug. 19, 2014

(65) Prior Publication Data

US 2015/0064776 A1 Mar. 5, 2015

Related U.S. Application Data

(60) Provisional application No. 61/870,362, filed on Aug. 27, 2013, provisional application No. 61/886,181, filed on Oct. 3, 2013.

(51) Int. Cl.
| | |
|---|---|
| *C12M 1/22* | (2006.01) |
| *C12Q 1/04* | (2006.01) |
| *C12M 1/00* | (2006.01) |
| *G01N 1/22* | (2006.01) |

(52) U.S. Cl.
CPC .............. *C12Q 1/04* (2013.01); *C12M 23/10* (2013.01); *C12M 23/38* (2013.01); *G01N 1/2208* (2013.01)

(58) Field of Classification Search
CPC ......... C12M 23/10; C12M 23/38; C12Q 1/04; G01N 1/2208
See application file for complete search history.

(56) References Cited

U.S. PATENT DOCUMENTS

| | | | |
|---|---|---|---|
| 4,775,628 A | 10/1988 | Takakura et al. | 435/298 |
| 5,262,326 A * | 11/1993 | Jaeger | C12M 23/10 |
| | | | 215/214 |
| 8,753,835 B2 | 6/2014 | Rebe | 435/34 |

(Continued)

FOREIGN PATENT DOCUMENTS

JP WO 2011118256 A1 * 9/2011 ........... G01N 1/2208

OTHER PUBLICATIONS

Juozaitis et al., Applied Environmental Microbiology, vol. 60, No. 3, p. 861-870, 1994.

(Continued)

*Primary Examiner* — William H Beisner
(74) *Attorney, Agent, or Firm* — Renner, Otto, Boisselle & Sklar, LLP

(57) ABSTRACT

Provided is a sample dish for detecting microbes. The sample dish includes a base having an opening extending therethrough, an outer side wall at the outer periphery of the base, and an inner side wall at the inner periphery of the base defined by the opening. The sample dish may be used in conjunction with a microbial test unit including a housing defining an internal cavity configured to contain a sample dish, the unit including a cuff extending from an outlet of the housing into the internal cavity. The cuff may be an open-ended member configured to extend through an opening of the sample dish and provide fluid communication between the internal cavity and the outlet. The microbial test unit provides the ability to test compressed gas directly input to the unit.

20 Claims, 11 Drawing Sheets

(56) References Cited

U.S. PATENT DOCUMENTS

2006/0257287 A1 11/2006 Call et al. .................. 422/83
2007/0056389 A1* 3/2007 Lai ..................... B01D 45/08
                                                            73/863.22
2011/0167931 A1 7/2011 Vellutato, Jr. ............ 73/863.11

OTHER PUBLICATIONS

Terzieva et al., Applied and Environmental Microbiology, vol. 62, No. 7, p. 2264-2272, 1996.
Lawrence et al., *Bacillus anthracis* Spores (Etiologic Agent of Anthrax) in Air, The National Occupational Research Agenda, p. 81-106, Salt Lake City, Utah: The University of Utah, 2003.
Dotson et al. (Proceedings: Indoor Air, 2002).
Zefon (Air-O-Cell brochure, http://www.zefon.com/store/air-o-cell-sampling-cassette.html, accessed Jan. 10, 2014).
Grinsphun et al. (Journal of Environmental Monitoring, vol. 9, p. 855-861, 2007).
International PBI S.p.A.; "Compressed Air/Gas Microbial Testing for Sterility Control in Clean Room According to ISO 8573-7"; Mar. 2009.
Biocompare; "Testing Compressed Air Lines for Microbiological Contamination"; May 2006.
PMV Air Samplers; "RCG Comp Gas/Confined Space Sampler"; 2009.

\* cited by examiner

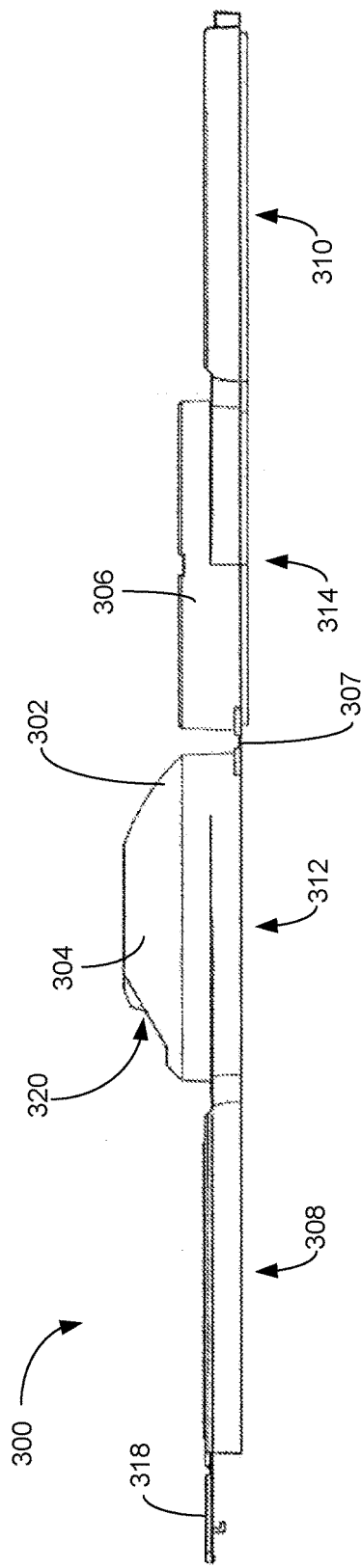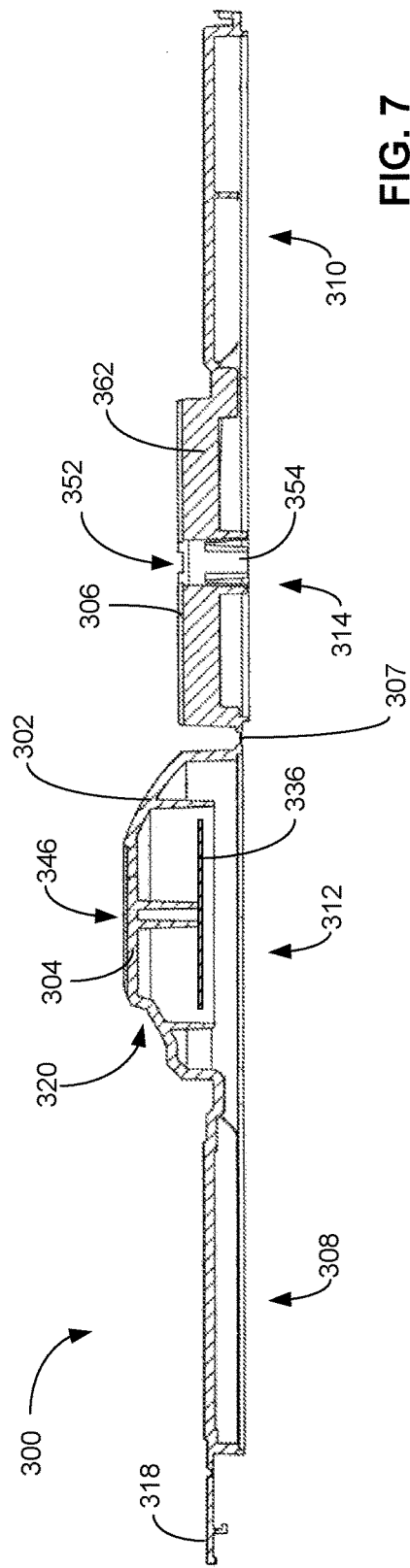

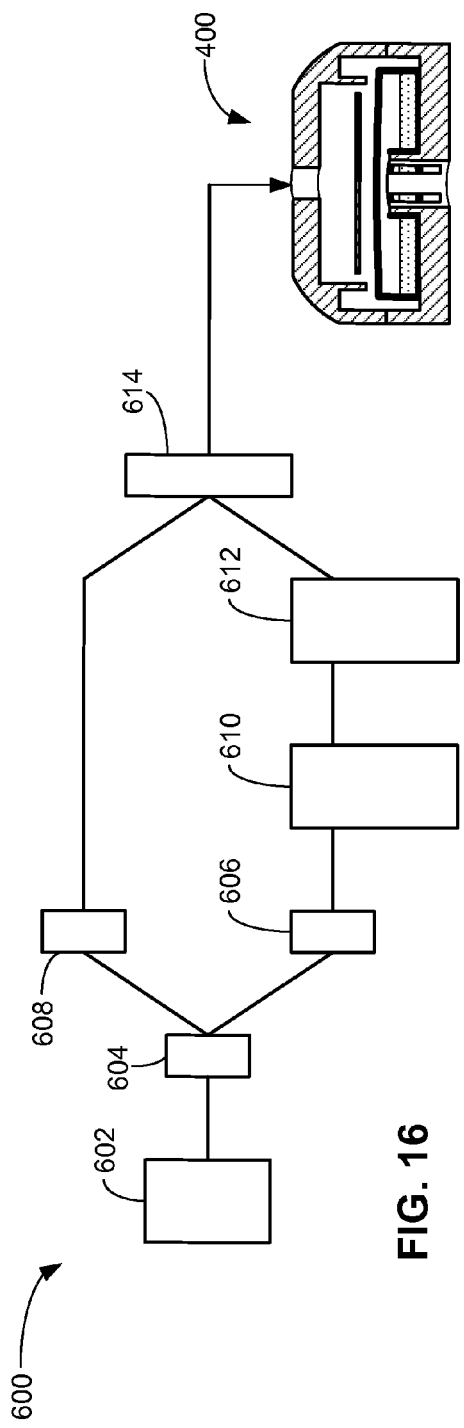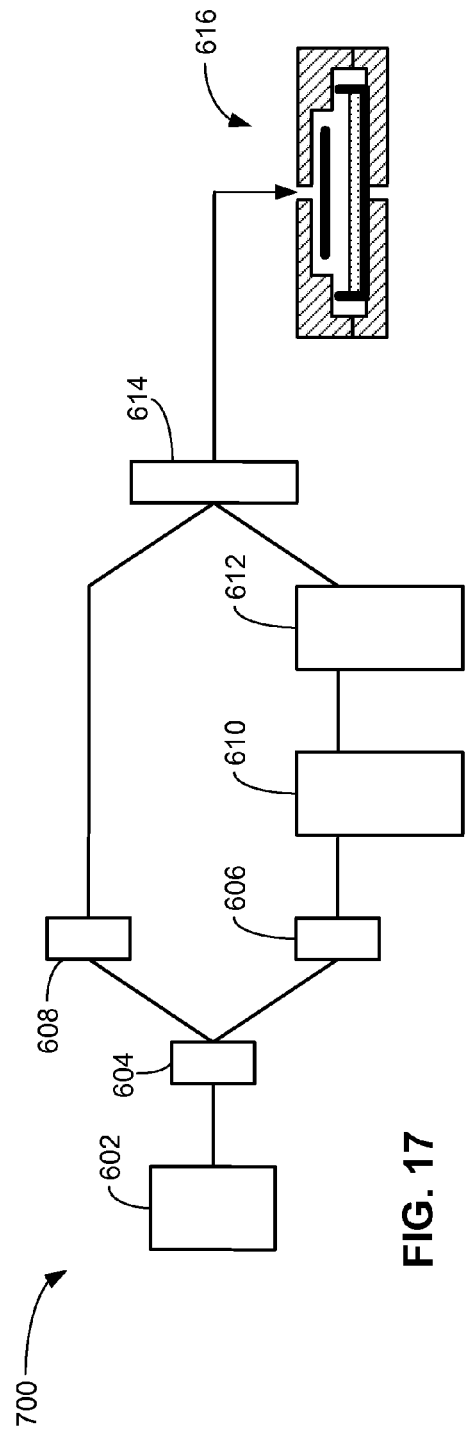

SAMPLE DISH AND COMPRESSED GAS MICROBIAL TEST UNIT

RELATED APPLICATIONS

This application claims the benefit of U.S. Provisional Application No. 61/870,362 filed Aug. 27, 2013, and claims the benefit of U.S. Provisional Application No. 61/886,181 filed Oct. 3, 2013, the disclosures of which are incorporated herein by reference in their entireties.

FIELD OF INVENTION

The present invention relates generally to microbial detection, and more particularly to a sample dish and compressed gas microbial test unit.

BACKGROUND

Compressed gas is used in a number of applications. For example, in the food industry, compressed air is used as an ingredient in whipped products such as ice cream and yogurt. Compressed air is also used as a processing tool to slice or cut soft food products and to open packages before filling with food product.

There is currently no standard method to evaluate the microbial content of compressed gas. This is particularly an issue in the food industry, as food manufacturers are under pressure to validate the safety of all ingredients and processes for regulatory compliance.

SUMMARY OF INVENTION

The present invention provides a sample dish for detecting microbes. The sample dish includes a base having an opening extending therethrough, an outer side wall at the outer periphery of the base, and an inner side wall at the inner periphery of the base defined by the opening. The sample dish may be used in conjunction with a microbial test unit including a housing defining an internal cavity configured to contain a sample dish, the unit including a cuff extending from an outlet of the housing into the internal cavity. The cuff may be an open-ended member configured to extend through an opening of the sample dish and provide fluid communication between the internal cavity and the outlet. The microbial test unit provides the ability to test compressed gas directly input to the unit. Both the sample dish and microbial test unit may further allow for improved air flow and distribution of the gas on the surface of a microbial growth substrate, which may allow for improved microbial detection.

According to one aspect of the invention, a sample dish includes: a base extending in a direction along a longitudinal axis between opposed first and second surfaces and extending radially outward in a direction orthogonal to the longitudinal axis, the base including an outer periphery extending between the opposed first and second surfaces, an opening extending through the base between the opposed first and second surfaces, and an inner periphery extending between the opposed first and second surfaces and defined by the opening; an outer side wall at the outer periphery of the base, the outer side wall extending from the first surface of the base in a direction along the longitudinal axis; and an inner side wall at the inner periphery of the base, the inner side wall extending from the first surface of the base in a direction along the longitudinal axis.

In an embodiment, the opening and the inner side wall are concentric with the outer periphery.

In another embodiment, the sample dish further includes at least one channel at the second surface of the base, the channel extending from the outer periphery to the inner periphery.

In yet another embodiment, the at least one channel extends linearly from the outer periphery to the inner periphery.

In a further embodiment, the first surface of the base, the outer side wall, and the inner side wall form a receptacle configured to hold a microbial growth substrate.

In a further embodiment, the sample dish further includes at least one partition wall extending from the first surface of the base in a direction along the longitudinal axis, the at least one partition wall arranged to divide the receptacle into two or more sub-regions.

According to another aspect of the invention, a microbial test unit includes: a housing extending along a longitudinal axis between a first end and a second end, the housing defining an internal cavity including a decompression region for decompressing compressed gas input to the internal cavity and a sampling region in fluid communication with the decompression region for containing a sample dish, the decompression region and the sampling region defining a flow path through the internal cavity; an inlet at a first end of the housing proximate the decompression region; an outlet at a second end of the housing proximate the sampling region; and a cuff extending along the longitudinal axis into the sampling region from the outlet, the cuff being an open-ended member configured to extend through an opening of the sample dish and provide fluid communication between the sampling region and the outlet.

In an embodiment, the microbial test unit further includes a plurality of ribs projecting into the sampling region along the longitudinal axis, each rib radially extending from the cuff to an inner surface of the housing, each of the plurality of ribs configured to mate with a respective channel of the sample dish.

In another embodiment, the microbial test unit further includes a flow channel provided between respective ones of the plurality of ribs, the flow channel radially extending between the cuff and the inner surface of the housing.

In yet another embodiment, the cuff includes an opening configured to provide fluid communication between the flow channel and the outlet.

In a further embodiment, a microbial test system includes: the microbial test unit; and a sample dish, including: a base extending in a direction along the longitudinal axis between opposed first and second surfaces and extending radially outward in a direction orthogonal to the longitudinal axis, the base including an outer periphery extending between the opposed first and second surfaces, an opening extending through the base between the opposed first and second surfaces, and an inner periphery extending between the opposed first and second surfaces and defined by the opening; an outer side wall at the outer periphery of the base, the outer side wall extending from the first surface of the base in a direction along the longitudinal axis; and an inner side wall at the inner periphery of the base, the inner side wall extending from the first surface of the base in a direction along the longitudinal axis.

In a further embodiment, the microbial test unit includes a plurality of ribs projecting into the sampling region along the longitudinal axis, each rib radially extending from the cuff to an inner surface of the housing; and the sample dish includes a plurality of channels at the second surface of the base, each of the channels extending from the outer periphery to the inner periphery, each of the channels configured to mate with a respective one of the plurality of ribs.

In a further embodiment, the microbial test unit further includes a flow channel provided between respective ones of the plurality of ribs, the flow channel radially extending between the cuff and the inner surface of the housing; the second surface of the base collectively forms a passage with the flow channel; and the cuff includes an opening configured to provide fluid communication between the passage and the outlet.

According to another aspect of the invention, a microbial test unit includes: a housing extending along a longitudinal axis between a first end and a second end, the housing defining an internal cavity configured to contain a sample dish; an outlet passing through the housing at the second end of the housing the bottom surface circumscribing the outlet; and a cuff extending along the longitudinal axis into the internal cavity from the outlet, the cuff being an open-ended member configured to extend through an opening of the sample dish and provide fluid communication between the internal cavity and the outlet.

In an embodiment, the microbial test unit further includes a plurality of ribs projecting into the internal cavity along the longitudinal axis, each rib radially extending from the cuff to an inner surface of the housing, each of the plurality of ribs configured to mate with a respective channel of the sample dish.

In another embodiment, the microbial test unit further includes a flow channel provided between respective ones of the plurality of ribs, the flow channel radially extending between the cuff and the inner surface of the housing.

In yet another embodiment, the cuff includes an opening configured to provide fluid communication between the flow channel and the outlet.

In a further embodiment, a microbial test system includes: the microbial test unit of claim 14; and a sample dish including: a base extending in a direction along the longitudinal axis between opposed first and second surfaces and extending radially outward in a direction orthogonal to the longitudinal axis, the base including an outer periphery extending between the opposed first and second surfaces, an opening extending through the base between the opposed first and second surfaces, and an inner periphery extending between the opposed first and second surfaces and defined by the opening; an outer side wall at the outer periphery of the base, the outer side wall extending from the first surface of the base in a direction along the longitudinal axis; and an inner side wall at the inner periphery of the base, the inner side wall extending from the first surface of the base in a direction along the longitudinal axis.

In a further embodiment, the microbial test unit includes a plurality of ribs projecting into the internal cavity along the longitudinal axis, each rib radially extending from the cuff to an inner surface of the housing; and the sample dish includes a plurality of channels at the second surface of the base, each of the channels extending from the outer periphery to the inner periphery, each of the channels configured to mate with a respective one of the plurality of ribs.

In a further embodiment, the microbial test unit further includes a flow channel provided between respective ones of the plurality of ribs, the flow channel radially extending between the cuff and the inner surface of the housing; the second surface of the base collectively forms a passage with the flow channel; and the cuff includes an opening configured to provide fluid communication between the passage and the outlet.

The foregoing and other features of the invention are hereinafter described in greater detail with reference to the accompanying drawings.

BRIEF DESCRIPTION OF THE DRAWINGS

FIG. 6 is a side view of the exemplary microbial test unit shown in FIG. 5 in an open state;

FIG. 7 is a cross-sectional side view of the exemplary microbial test unit shown in FIG. 5 in an open state;

FIGS. 16 and 17 are schematic diagrams showing experimental bacterial nebulization and sampling systems.

DETAILED DESCRIPTION

Figure 1:
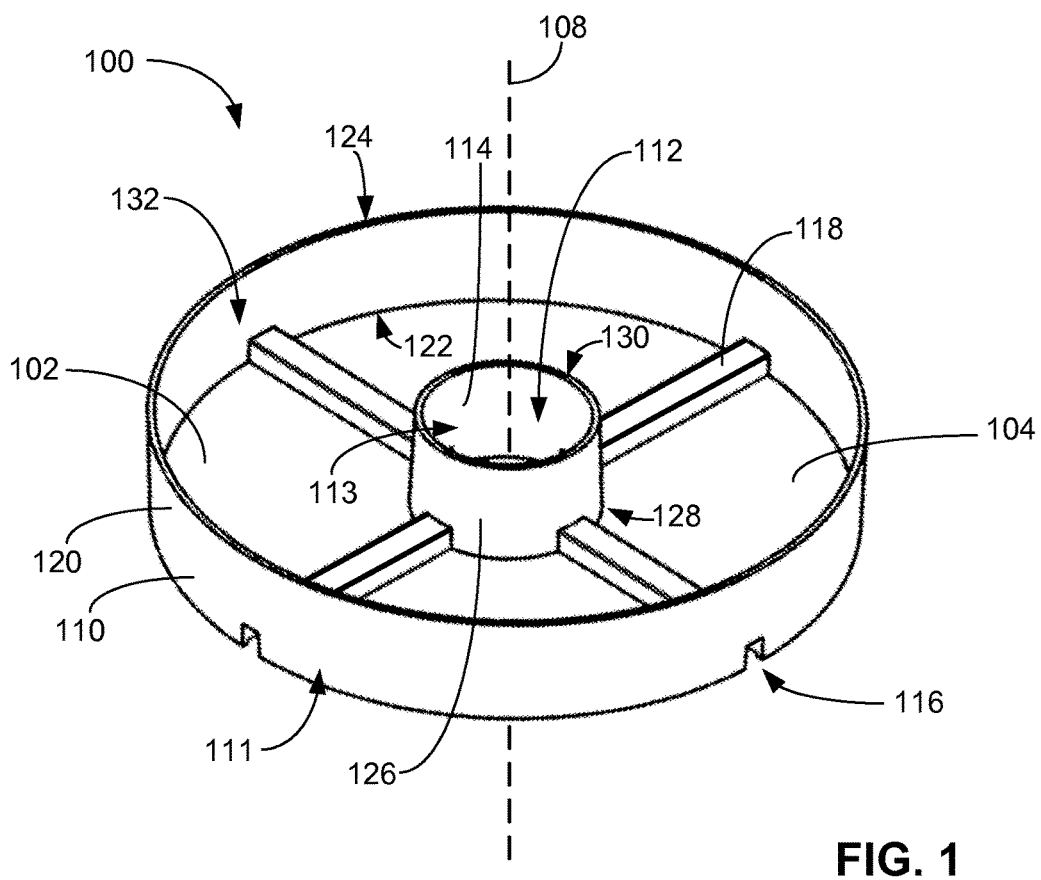
FIG. 1 is a perspective view of an exemplary sample dish.
Figure 2:
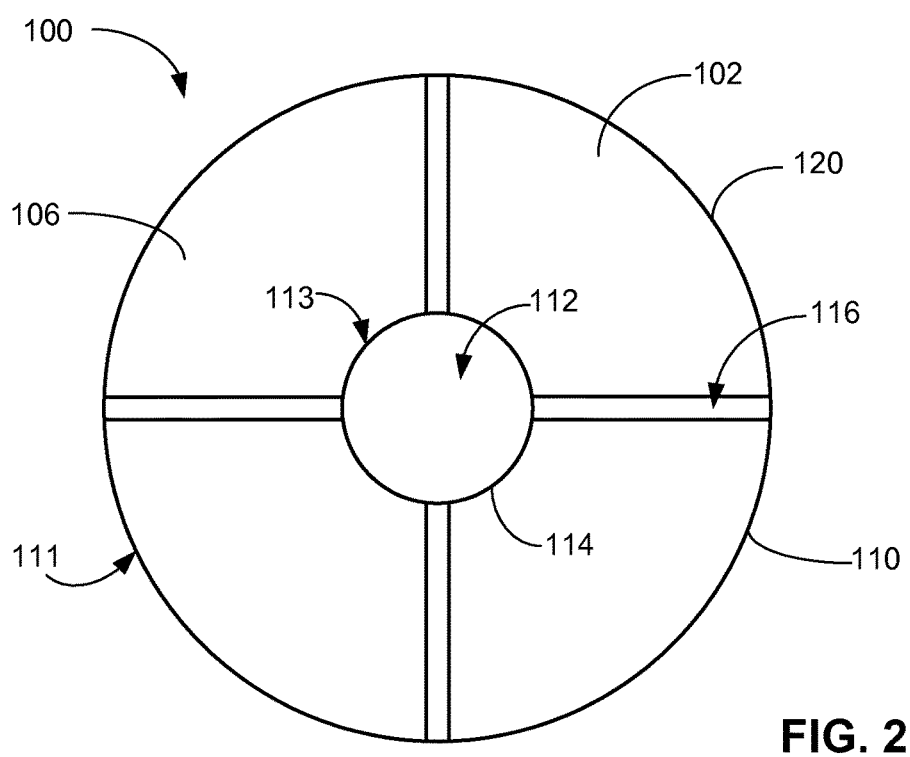
FIG. 2 is a bottom view of the exemplary sample dish shown in FIG. 1.

The principles of the present application have particular application to detecting microbes in a compressed gas (e.g., compressed air), and thus will be described below chiefly in this context. It will of course be appreciated, and also understood, that the principles of the invention may be useful for other gasses (e.g., nitrogen, oxygen, carbon dioxide, etc.). The principles of the invention may be used for one or more applications (e.g., foods, cosmetics, beverages, biotech applications, etc.) where microbial detection is desired.

Referring now in detail to the drawings and initially to FIGS. 1 and 2, a sample dish is illustrated generally at 100. The sample dish is configured to hold a microbial growth substrate. The sample dish may be formed from any suitable material (e.g., glass, polymeric material, etc.), and may be formed by any suitable process (e.g., molding). The microbial growth substrate may be any suitable substrate for collecting and culturing microbes. In some embodiments, the microbial growth substrate is an agar substrate. Depending on the particular kind of microbe(s) to be detected, a suitable microbial growth substrate may be selected. Examples of suitable microbial growth substrates include tryptic soy medium, Rose Bengal-Streptomycin agar medium, potato dextrose medium, blood agar medium, chocolate agar medium, BTB lactose agar medium, DHL agar medium, SS agar medium, isolation medium for anaerobic bacterium, medium for enrichment, and the like. The agar substrate may be mixed with any suitable nutrient media for promoting growth of collected microbes.

The sample dish 100 includes a base 102. The base 102 includes a first surface 104 and a second surface 106 opposite the first surface 104. The base 102 extends between the first surface 104 and the second surface 106 in a thickness direction extending along a longitudinal axis 108. The base 102 also extends in a width direction orthogonal to the longitudinal axis 108. As shown, the base 102 extends radially from the longitudinal axis 108.

The base 102 includes at least one outer edge surface 110 extending between the first surface 104 and the second surface 106. The outer edge surface 110 defines an outer periphery 111 of the base 102. In the embodiment shown, the outer edge surface 110 of the base 102 defines a circular outer periphery. In other embodiments, the outer periphery of the base 102 may be another suitable shape (e.g., a rectangle, square, oval, triangle, polygon, etc.) as defined by one or more edge surfaces. Individual edges that form the outer periphery of the base 102 will be collectively referred to herein as the outer edge surface.

An opening 112 extends through the base 102 between the first surface 104 and the second surface 106. As shown, the opening 112 may be centrally located relative to (e.g., concentric with) the outer periphery (the outer edge surface 110). In other embodiments, the opening 112 may be offset from a center of the base 102 relative to the outer periphery (the outer edge surface 110).

The base 102 includes at least one inner edge surface 114 extending between the first surface 104 and the second surface 106. The inner edge surface 114 defines the shape of the opening 112 as well as an inner periphery 113 of the base 102. In the embodiment shown, the inner edge surface 114 of the base 102 defines a circular inner periphery. Accordingly, the opening 112 is circular (e.g., annular) in shape. In other embodiments, the inner periphery of the base 102 and the opening 112 may be another suitable shape (e.g., a rectangle, square, oval, triangle, polygon, etc.) defined by one or more edge surfaces. The individual edge surfaces that form the inner periphery of the base will be collectively referred to as an inner edge surface. In some embodiments, the shape of the inner periphery 113 may be different than the shape of the outer periphery 111. For example, although not specifically shown, the outer periphery may be circular in shape and the inner periphery may be rectangular in shape.

The base 102 may include one or more channels 116 extending between the inner edge surface 114 (inner periphery 113) and the outer edge surface 110 (outer periphery 111). Each channel 116 may be formed as an indentation at the second surface 106 of the base 102. In some embodiments, and as shown in the figures, a protrusion 118 corresponding to the indentation may be present at the first surface 104 of the base 102. Although in other embodiments, the thickness of the base 102 may allow for no protrusion to be provided at the first surface 104. As described below, in some embodiments, the one or more channels 116 may assist in the alignment of the sample dish when placed in a microbial test unit. In other embodiments, the one or more channels may assist in directing air flow toward an exit of a microbial test unit.

In the embodiment shown, the channels 116 extend radially outward from the opening in a direction orthogonal to the longitudinal axis 108. The channels 116 are shown as linear channels. In other embodiments (not shown), the channels 116 may each have a curved shape. This may provide a more tortuous path in embodiments where the one or more channels assist in directing air flow toward an exit of a microbial test unit. In some examples, each of the channels 116 has the same shape. In other examples, the channels may have different respective shapes. This may allow for a specific alignment of the sample dish 100 in the microbial test unit.

The sample dish 100 includes an outer side wall 120 at the outer periphery 111 of the base 102. The outer side wall 120 extends from the first surface 104 of the base in a direction along the longitudinal axis 108 between a proximal end 122 and a distal end 124 and follows the outer periphery 111 of the base. In the embodiment shown, the outer side wall 120 extends between the proximal end 122 and the distal end 124 in a direction that is nominally parallel to the longitudinal axis 108. In other embodiments, the outer side wall 120 may extend between the proximal end 122 and the distal end 124 at an angle relative to the longitudinal axis 108.

The sample dish 100 includes an inner side wall 126 at the inner periphery 113 of the base 102. The inner side wall 126 extends from the first surface 104 of the base 102 in a direction along the longitudinal axis 108 between a proximal end 128 and a distal end 130 and follows the inner periphery 113 of the base. In the embodiment shown, the inner side wall 126 extends between the proximal end 122 and the distal end 124 in a direction that is nominally parallel to the longitudinal axis 108. In other embodiments, the inner side wall 126 is tapered such that it extends between the proximal end 122 and the distal end 124 at an angle relative to the longitudinal axis 108. The inner side wall 126 may be shaped to form a seal between the inner side wall 126 and a cuff of a microbial test unit. Accordingly, in some embodiments, the inner side wall 126 may also be referred to as a sealing wall.

Figure 13:
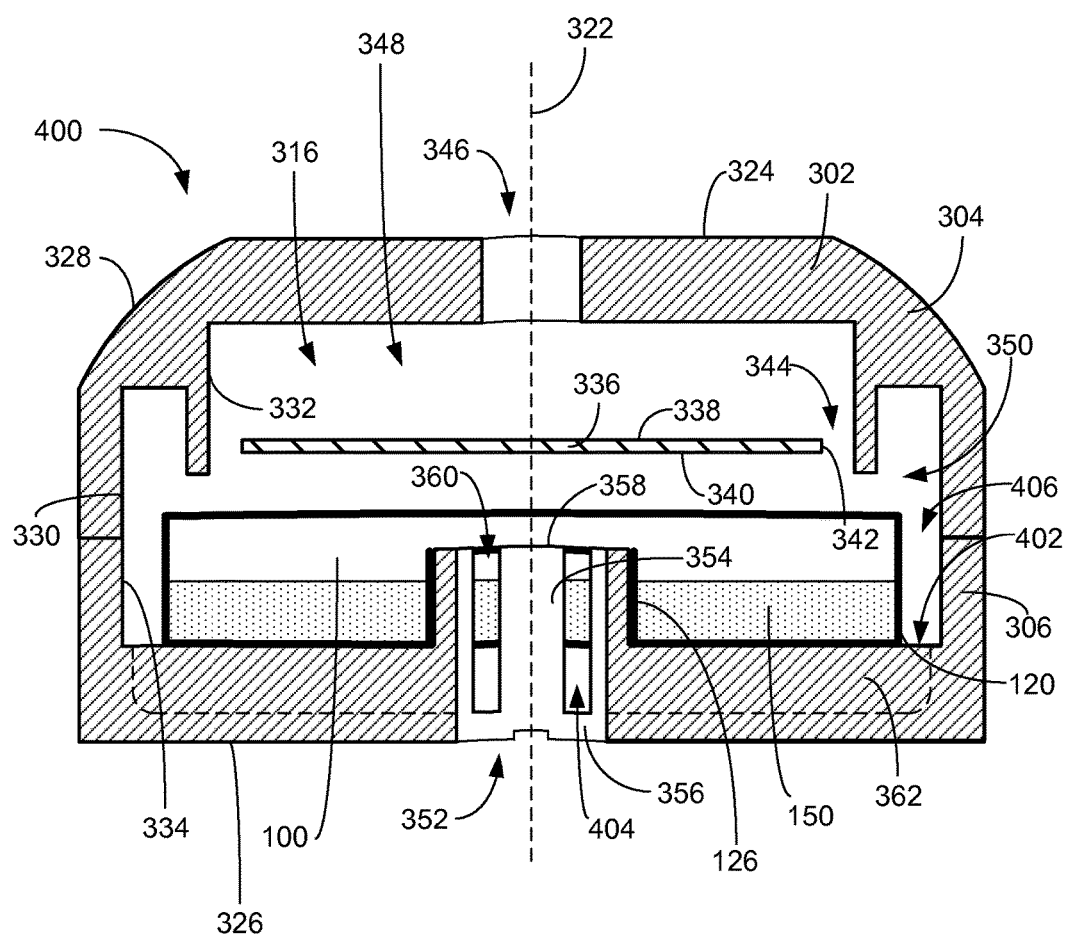
FIG. 13 is a schematic cross-sectional side view of parts of an exemplary microbial test system.

The base 102, together with the outer side wall 120 and inner side wall 126, collectively form a receptacle region 132 configured to hold a microbial growth substrate (shown in FIG. 13 as element 150).

The sample dish 100 may be any suitable size. In some embodiments, the sample dish is the size of a standard size Petri dish. For example, the base 102 may have a diameter of about 3.5 inches and the outer side wall 120 and inner side wall 126 may have a height of about 0.6 inch. The size of the opening may be any suitable size. As described below, when the sample dish is installed in a microbial test unit, the opening 112 may receive a cuff of the microbial test unit and may allow for sample air to pass therethrough and exit the microbial test unit. Accordingly, the size of the opening 112 may correspond to the dimensions of a cuff of the microbial test unit, and may also be of sufficient size to permit a sufficient amount of air to pass therethrough.

Figure 3:
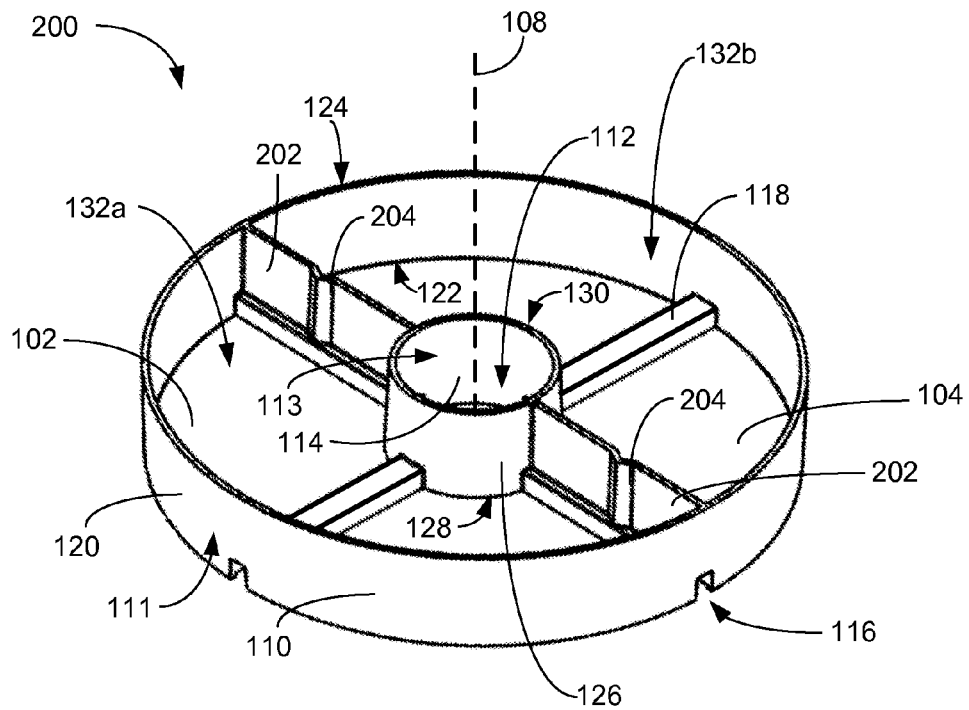
FIG. 3 is a perspective view of another exemplary sample dish.
Figure 4:
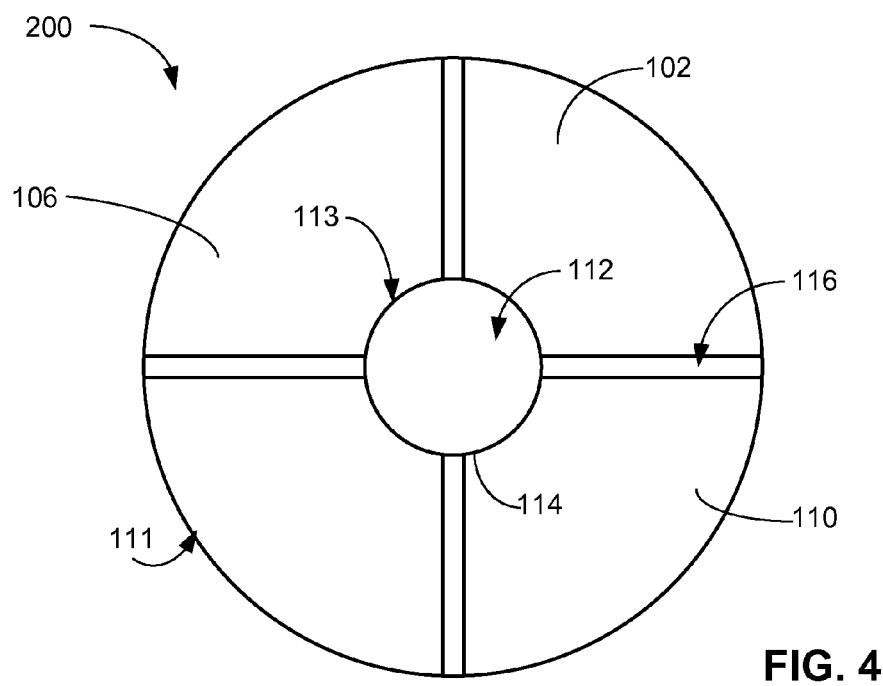
FIG. 4 is a bottom view of the another exemplary sample dish shown in FIG. 3.

Referring now to FIGS. 3 and 4, another exemplary sample dish is shown at 200. The sample dish 200 is similar to the sample dish 100, but includes at least one partition wall 202. The partition wall(s) 202 may allow for the sample dish to be divided into two or more receptacle sub-regions for retaining microbial growth substrates. For example, the sample dish 200 shown in FIGS. 3 and 4 includes two partition walls 202, which collectively define two sub-regions 132a, 132b for containing microbial growth substrates. This may allow for the use of more than one type of microbial growth substrate with the sample dish 200, thereby improving the versatility of the sample dish. For example, one microbial growth substrate may be suited for culturing one type of microbe, whereas another microbial growth substrate may be suited for culturing another type of microbe. By including both microbial growth substrates, a single sample dish may be used for testing the presence of both types of microbes. In other embodiments, the sample dish may include more than two partition walls, which may result in the presence of more than two sub-regions and may allow for the use of more than two types of microbial growth substrates.

In some embodiments, one or more of the partition walls 202 may include a feature that enables a user to distinguish one sub-region from another. In the example shown, each partition wall 202 includes a notch 204 pointing toward one of the sub-regions (e.g., sub-region 132a). With this arrangement, a user can distinguish the one sub-region from the other.

The sample dish 100, 200 may be used together with any suitable microbial test unit (e.g., a microbial test unit and the sample dish being collectively referred to as a microbial test system). Exemplary microbial test units suitable for used with the sample dish are described in U.S. Pat. No. 8,753,835, the disclosure of which is incorporated herein by reference in its entirety.

Referring now in detail to FIGS. 5-12, an exemplary microbial test unit is illustrated generally at 300. The microbial test unit 300 may be used together with the sample dish 100, 200 in testing for the presence of microbes in a compressed gas.

The microbial test unit 300 includes a housing 302. The housing 302 includes a first portion 304 and a second portion 306. The first portion 304 may be attached to and movable relative to the second portion 306. In the example shown, the microbial test unit 300 includes a hinge 307 joining the first portion 304 with the second portion 306 that effectuates opening and closing of the housing 302.

Figure 5:
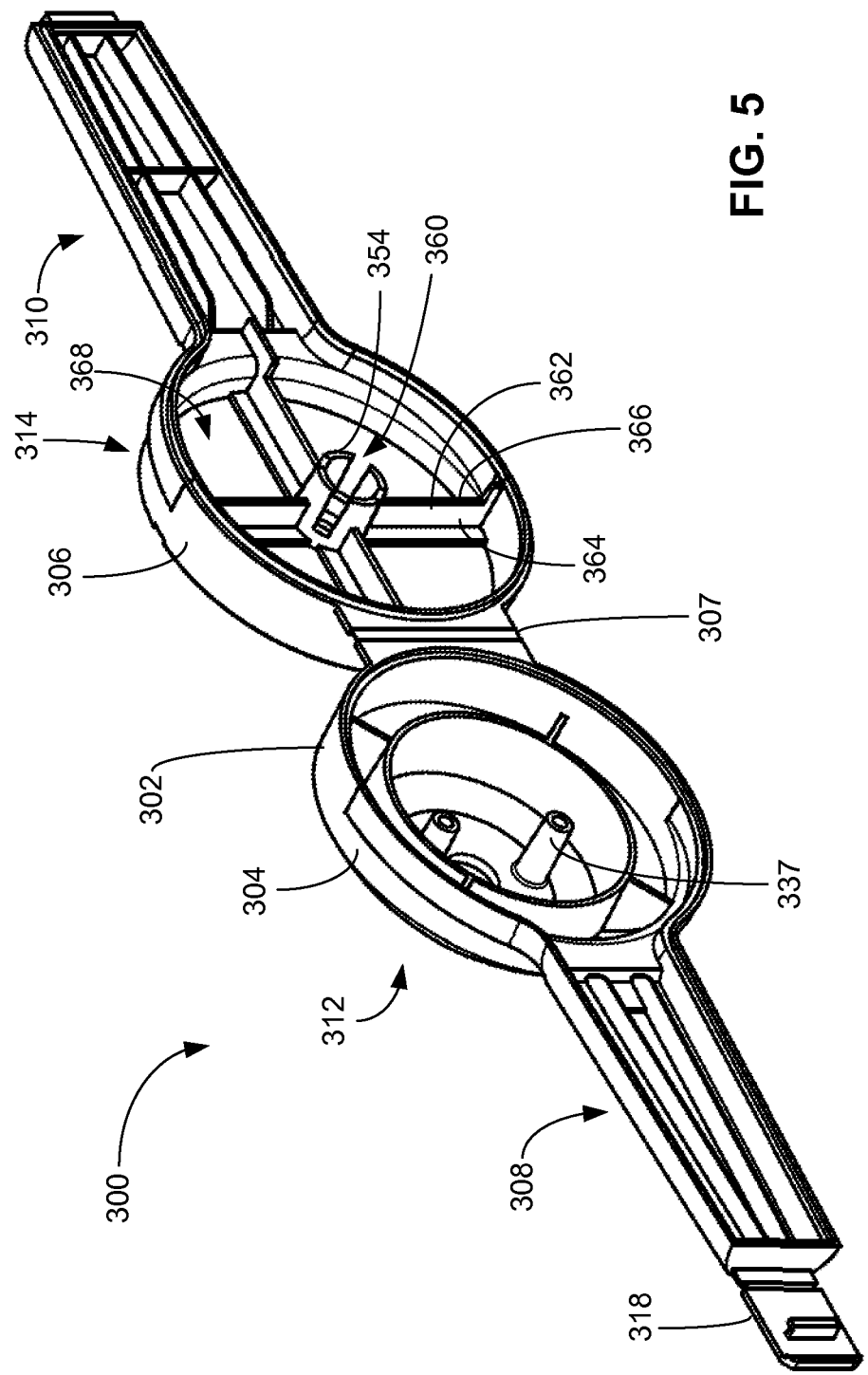
FIG. 5 is a perspective view of an exemplary microbial test unit in an open state.
Figure 8:
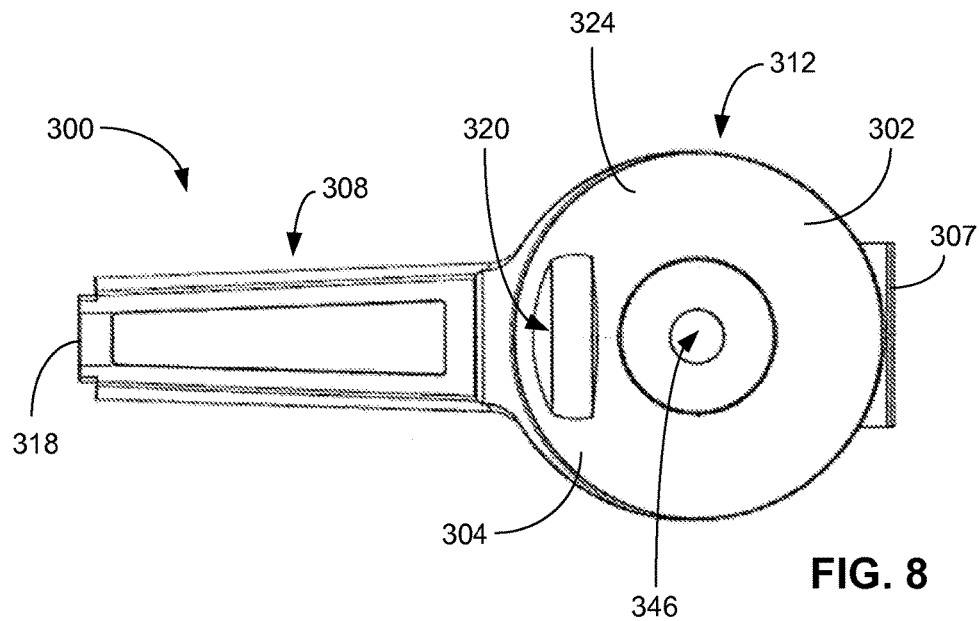
FIG. 8 is a top view of the exemplary microbial test unit shown in FIG. 5 in a closed state.
Figure 9:
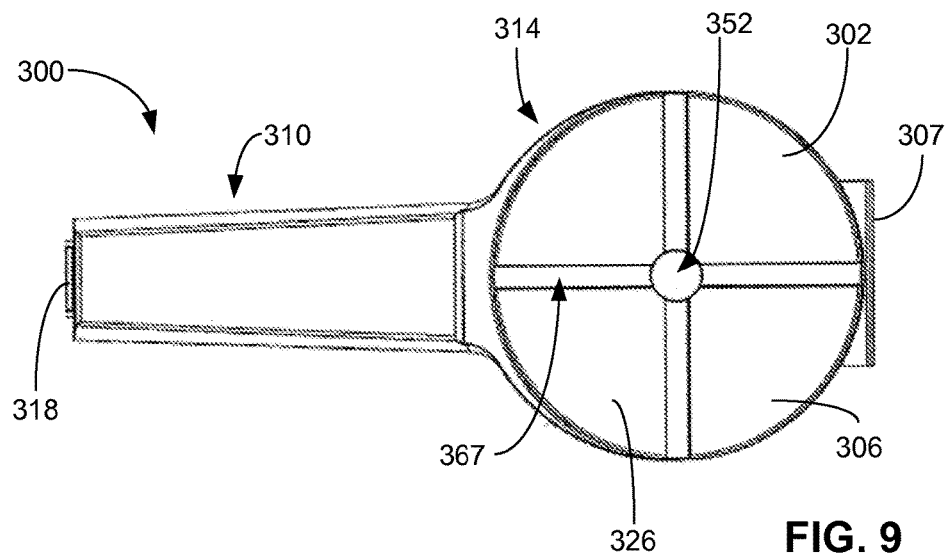
FIG. 9 is a bottom view of the exemplary microbial test unit shown in FIG. 5 in a closed state.
Figure 10:
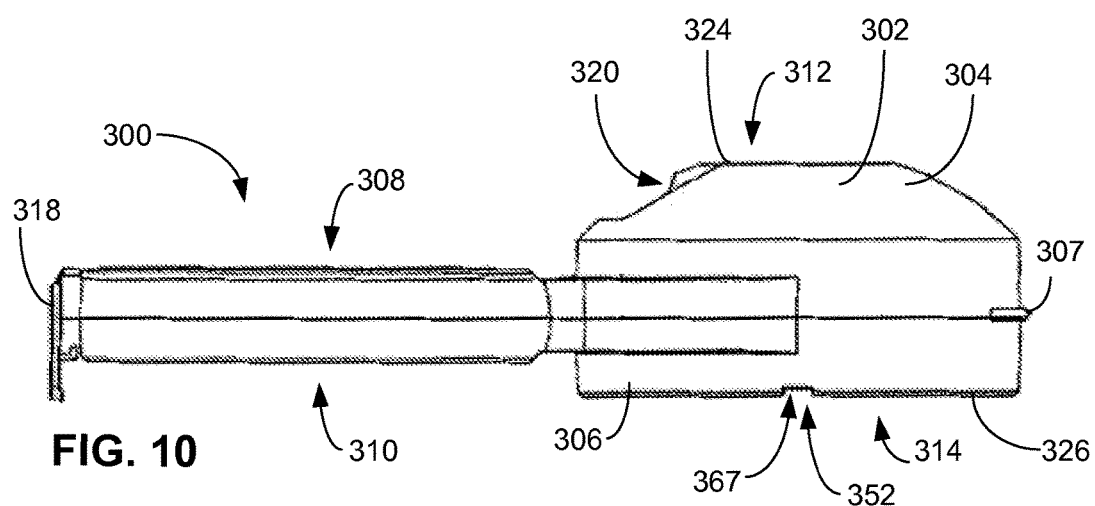
FIG. 10 is a side view of the exemplary microbial test unit shown in FIG. 5 in a closed state.
Figure 11:
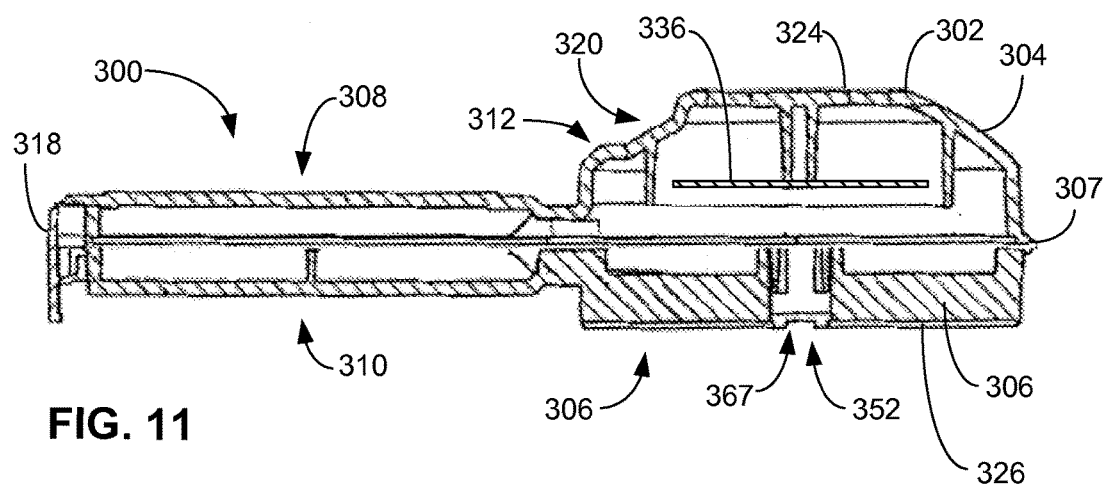
FIG. 11 is a cross-sectional side view of the exemplary microbial test unit shown in FIG. 5 in a closed state.

FIGS. 5-7 show the microbial test unit 300 in an open position. Each portion 304, 306 includes a handle segment 308, 310 and an internal cavity segment 312, 314. The respective handle segments 308, 310 may help facilitate closing of the microbial test unit 300.

Figure 12:
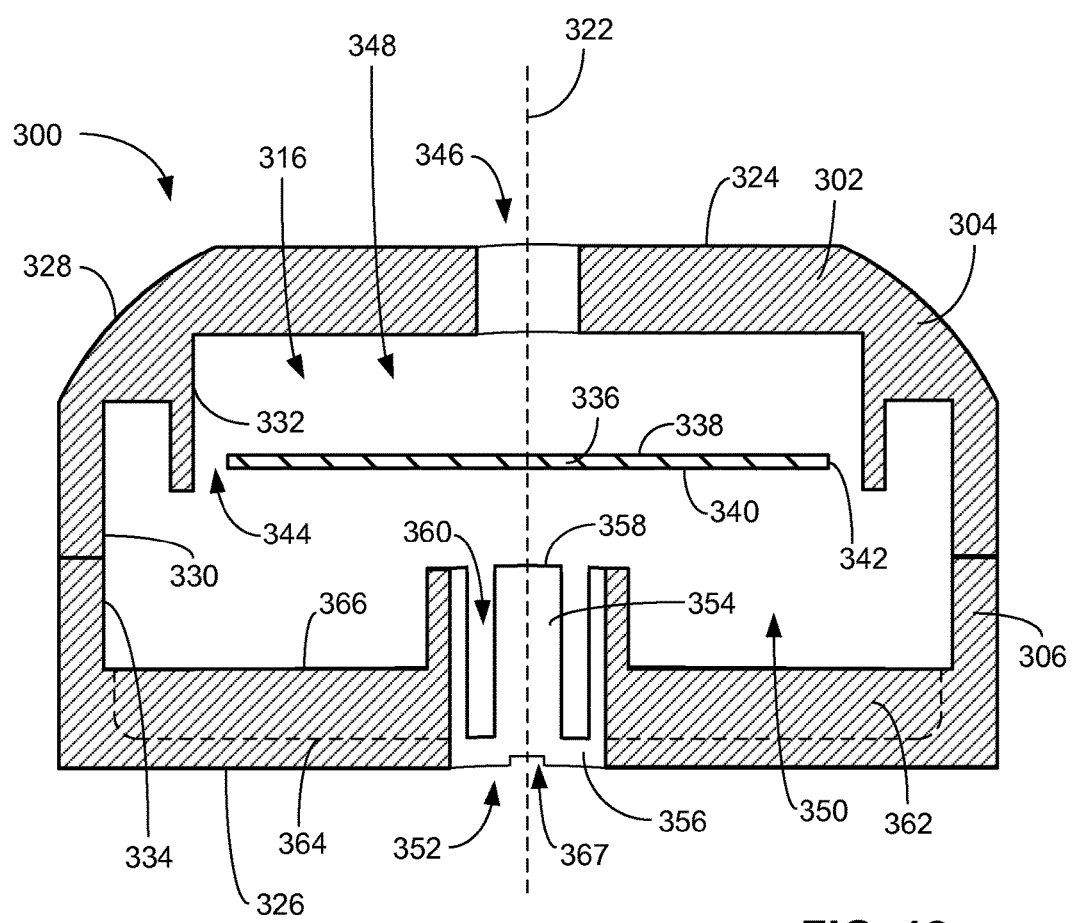
FIG. 12 is a schematic cross-sectional side view of parts of the exemplary microbial test unit shown in FIG. 5.

FIGS. 8-12 show the microbial test unit 300 in a closed position. In the closed position, the respective internal cavity segments 312, 314 of the first portion 304 and the second portion 306 collectively form the inner cavity 316 (FIG. 12). The handle segments 308, 310 of the first housing portion 304 and second housing portion 306 may include a locking mechanism 318 for retaining the first housing portion 304 and the second housing portion 306 in the closed position. In other embodiments, the microbial test unit 300 may include a plurality of locking mechanisms disposed about the outer periphery of the housing 302.

In some embodiments, the housing includes an additional handle 320. In the embodiment shown, an additional handle 320 is formed as a part of the first housing portion 304. The additional handle 320 may help facilitate opening the microbial test unit 300.

With specific reference to FIG. 12, in the closed position, the housing 302 (e.g., the first portion 304 and the second portion 306 of the housing 302 that collectively form the inner cavity 316) defines a longitudinal axis 322 extending between a first end 324 and a second end 326. The housing 302 includes an outer surface 328 and an inner surface 330 opposite the outer surface 328. The outer surface 328 extends along the longitudinal axis 322 between the first end 324 and the second end 326 of the housing 302. The inner surface 330 extends along at least a portion of the longitudinal axis 322, the periphery thereof defining the shape of the internal cavity 316. In the example shown, the periphery of the inner surface 330 extending along the longitudinal axis 322 is generally cylindrical in shape. In other embodiments, the periphery of the inner surface may be another suitable shape such as a rectangular prism or polygonal prism.

In some embodiments, the inner surface 330 of the housing 302 is a stepped surface extending along the longitudinal axis 322. As shown specifically in FIG. 12, the stepped inner surface 330 includes a first stepped portion 332 proximate the first end 324 of the housing 300 and a second stepped portion 334 proximate the second end 326 of the housing 302. The periphery of the second stepped portion 334 is larger than the periphery of the first stepped portion 332. In one embodiment, the periphery of the first stepped portion 332 may be generally cylindrical in shape and may have a diameter from about 2.0 inches to about 3.0 inches. In another embodiment, the periphery of the first stepped portion 332 may be generally cylindrical in shape and may have a diameter of about 2.5 inches. In one embodiment, the periphery of the second stepped portion 334 may be generally cylindrical in shape and may have a diameter from about 3.75 inches to about 4.75 inches. In another embodiment, the periphery of the second stepped portion 334 may be generally cylindrical in shape and may have a diameter of about 4 inches. The periphery of the first stepped portion 332 and the periphery of the second stepped portion 334 may be any suitable size.

A plate 336 is disposed in the internal cavity 316. The plate 336 includes opposed surfaces 338, 340 and at least one edge surface 342 extending between the opposed surfaces 338, 340. At least one of the surfaces 338, 340 of the plate 128 may be nominally perpendicular to the longitudinal axis 322. Although in other embodiments, at least one of the surfaces 338, 340 of the plate may be arranged at another suitable angle relative to the longitudinal axis 322. The surface 338 of the plate 336 is spaced apart from the inner surface 322 of the housing 302 proximate the first end 324. In some embodiments where the inner surface 332 of the housing 302 is a stepped surface, the spacing does not extend beyond the first stepped portion 332. The plate may be attached to the housing 302, for example, by mechanically fastening the plate to the first portion of the housing. FIG. 5 shows the first portion 302 of the housing 302 with the plate 336 removed to show an example of fastening members 337 for mechanically fastening the plate.

The at least one edge surface 342 defines the outer periphery of the plate 336. In the embodiment shown, the edge surface 342 defines a cylindrical periphery. In other embodiments, the edge surface 342 defines another suitable shape such as a rectangular or polygonal shape. The periphery of the plate 128 may have a shape similar to or different from the periphery of the inner surface 332 of the housing 302. A gap 344 is present between the at least one edge surface 342 of the plate 336 and the inner surface (e.g., the first stepped surface 332) of the housing 302. In the example shown, the gap 344 is an annular gap. In other embodiments, the size and shape of the gap 344 may depend on the size and shape of the outer periphery of the plate 336, and the size and shape of the periphery of the inner surface 332. In one embodiment, the gap 344 may be an annular gap and the distance between the inner surface 332 and the edge surface 342 of the plate that defines the gap may be from about 0.25 inch to about 0.75 inch.

The housing 302 includes an inlet 346 at the first end 324. Although not specifically shown, the inlet 346 may include a connector for connecting the microbial test unit 300 to a compressed gas source. Any suitable connector may be used, such as a quick-connect or threaded connector. The flow rate of the compressed gas into the microbial test unit 300 may be defined at least in part by the size of the inlet 346. The size of the inlet 346 may be any suitable size, e.g., to provide a suitable compressed gas flow rate. In one embodiment, the size of the inlet 346 may range from about 0.25 inch to about 1 inch. In another embodiment, the size of the inlet 346 may range from about 0.5 inch to about 0.75 inch. In yet another embodiment, the size of the inlet 346 may be about 0.7 inch.

The internal cavity 316 includes a decompression region 348 proximate the inlet 346 at the first end 324 of the housing 302. The decompression region 348 of the internal cavity 316 is at least partially defined by a portion of the inner surface 330 (e.g., by the first stepped portion 332) and by the surface 338 of the plate 336. The inlet 346 communicates with the decompression region 348 such that compressed gas entering the decompressing region 348 from the inlet 346 is incident on the surface 338 of the plate 336. As described in more detail below, the plate 336 is configured to direct the compressed gas incident on the plate 336 radially outward with respect to the longitudinal axis 322, thereby effectuating decompression of the compressed gas.

The internal cavity 316 additionally includes a sampling region 350 proximate the second end 326 of the housing 302. The sampling region 350 is separated from the decompression region 348 by the plate 336, and is at least partially defined by a portion of the inner surface 330 (e.g., the second stepped portion 334) and by the surface 340 of the plate 336. The sampling region 350 is suitable for containing the sample dish 100, 200. Separation of the first housing portion 304 and the second housing portion 306 provides access to the sampling region 350 and any sample dish disposed therein.

The gap 344 formed between the inner surface 330 (e.g., the first stepped portion 332) and the edge surface 342 of the plate 336 provides for fluid communication between the decompression region 348 and the sampling region 350. The gap 344 forms a passageway through which decompressed gas may pass from the decompression region 348 into the sampling region 350.

The housing 302 includes an outlet 352 at the second end 326. In the example shown, the outlet 352 is a circular orifice. In other embodiments, the outlet may be any suitable size and shape. The outlet 352 may output the gas from the housing 302 to the atmosphere. Although not specifically shown, in some embodiments the outlet 352 may include a suitable connector (e.g., a quick-connect or threaded connector) for connecting to a receptacle to collect the gas passed through the microbial test unit 300.

A cuff 354 extends from the outlet 352 into the sampling region 350 in a direction along the longitudinal axis 322. As described below, the cuff 354 is configured to extend through the opening of a sample dish inserted in the sampling region 350. The cuff 354 is an open-ended member that extends between a proximal end 356 and a distal end 358. In the embodiment shown, the cuff 354 extends between the proximal end 356 and the distal end 358 in a direction nominally parallel to the longitudinal axis 322. In other embodiments, the cuff 354 may be tapered between the proximal end 356 and the distal end 358. In some embodiments, the cuff 354 may form a seal with the inner side wall of the sample dish (and may also be referred to as a sealing cuff). The cuff 354 may also provide fluid communication between the internal cavity (e.g., the sampling region) and the outlet of the microbial test unit.

The sampling region 350 includes a plurality of ribs 362 projecting into the sampling region along the longitudinal axis 322 between a proximal end 364 and a distal end 366. In the embodiment shown, each rib 362 also extends radially from the cuff 354 to the inner surface 330 (e.g., the second stepped portion 334). In those embodiments where the sample dish 100, 200 includes channels 116, the distal end 366 of each rib 362 may be configured to mate with a respective channel 116 of the sample dish. Accordingly, the shape of the rib extending from the cuff 354 to the inner surface 330 may correspond to the shape of the channel. When the sample dish 100, 200 is provided in the sampling region 350 of the microbial test unit 300, the second surface 106 of the base 102 may be supported by the distal end 366 of the ribs 362.

The areas between the ribs 362 define respective flow channels 368 (FIG. 5). Each flow channel 368 extends between the inner surface 330 (e.g., the second stepped portion 334) and the cuff 354. The shape of each flow channel 368 may depend on the shape of the ribs 362. In the example shown, where the ribs extend linearly between the cuff 354 and the inner surface 330, each flow channel may be tapered such that it decreases in width as it extends from the inner surface 330 (e.g., the second stepped portion 334) to the cuff 354.

The flow channel may terminate at the cuff 354. The cuff 354 may include one or more openings 360 extending therethrough. The one or more openings 360 may allow for air flowing through a flow channel 368 to exit to the outlet. In the example shown, each opening 360 is rectangular in shape and extends between the proximal end 356 and the distal end 358 of the cuff. In other embodiments, the one or more openings may have any suitable shape and/or may extend only a portion of the distance between the proximal end 356 and the distal end 358 of the cuff 354.

The outer surface 328 of the second housing portion 306 may include one or more channels 367 extending radially from the outlet 352 in a direction orthogonal to the longitudinal axis 322. Each channel 367 may be formed as an indentation at the second end 326 of the housing 302. The one or more channels 367 may assist in directing air flow that exits the microbial test unit. For example, the microbial test unit may be placed on a flat surface and the testing may be conducted. Air exiting the outlet 352 may pass through the channels 367.

Referring now to FIG. 13, an exemplary microbial test system is shown at 400. The microbial test system includes the microbial test unit 300. In addition, the sample dish 100 is disposed in the sampling region 350. The sample dish 100 includes a microbial growth substrate 150 disposed therein. The sample dish is positioned such that the decompressed gas passing through the gap 344 into the sampling region 350 is incident on the microbial growth substrate 150.

When a sample dish is placed in the sampling region 350 and the channels 116 of the sample dish 100, 200 mate with the respective ribs 362, a gap 406 may be formed between the outer periphery 111 of the sample dish and the inner surface 330 (e.g., the second stepped portion 334) of the sampling region 350. The base 102 of the sample dish 100 closes off a portion of the flow channels 368 to form radially extending passages. The portion of each extending flow channel 368 that radially extends beyond the base 102 constitutes a passage inlet 402. The portion of each channel terminating at the outlet constitutes a passage outlet 404. The passage inlet 402 is in fluid communication with the sampling region 350 by the gap 406 formed between the sample dish and the inner surface of the housing 302. The gap 406 effectuates passage of the sampled gas into the radially extending passages.

Figure 14:
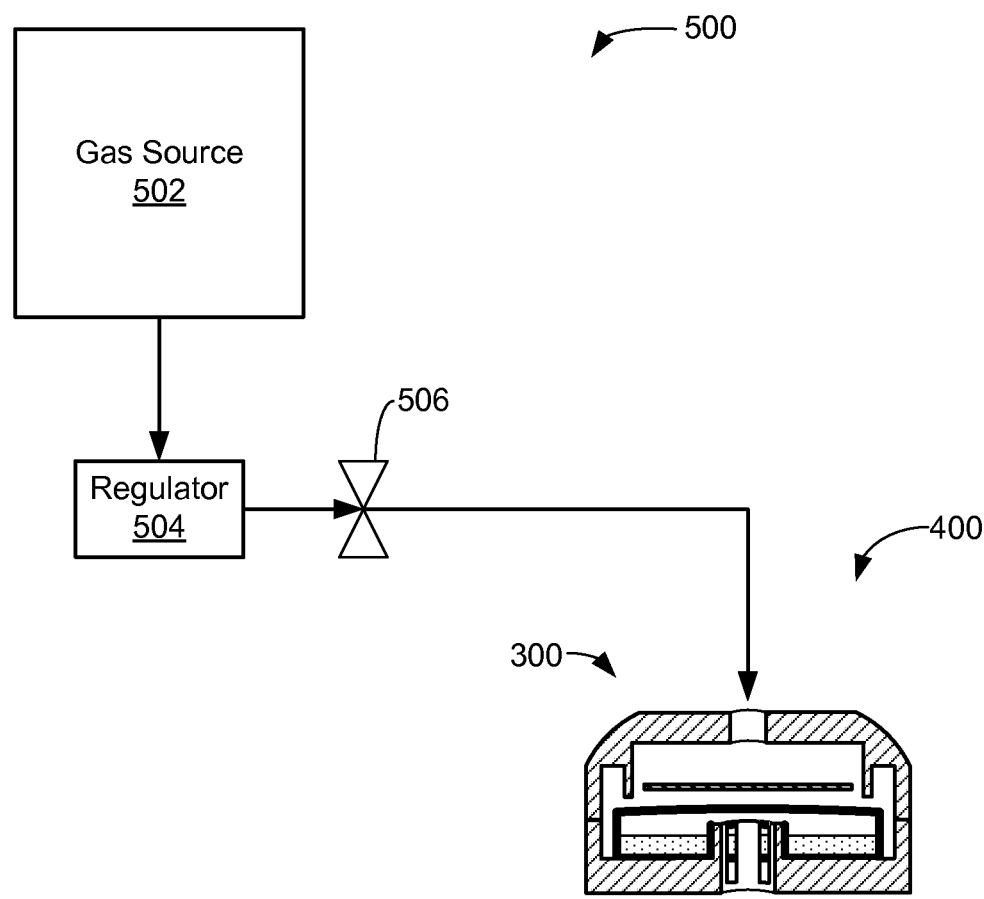
FIG. 14 is a schematic diagram showing an exemplary compressed gas system including an exemplary microbial test system.
Figure 15:
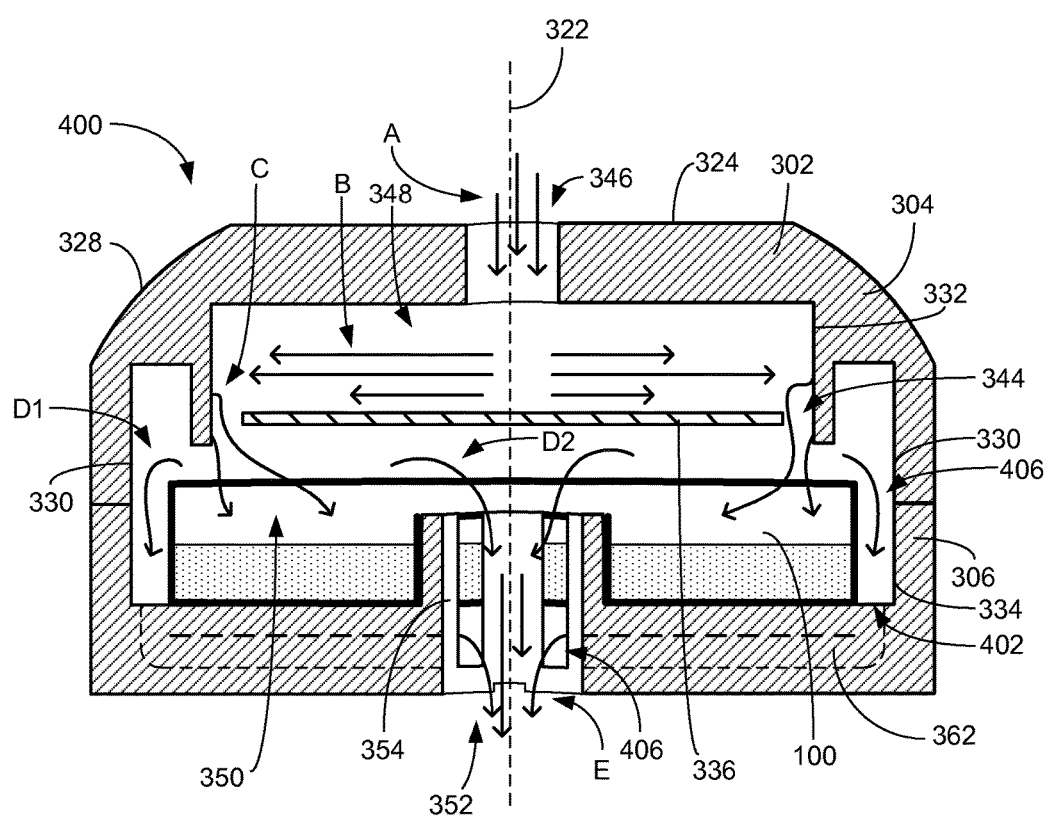
FIG. 15 is a schematic cross-sectional view showing the flow of gas through an exemplary microbial test system.

Referring now to FIG. 14, a compressed gas system including the microbial test system 400 is shown at 500. A gas source 502 is in fluid communication with the inlet of the microbial test unit 300. In one embodiment, the gas source is compressed air suitable for use in the food manufacturing industry. In other embodiments, the gas may be another type of gas (e.g., nitrogen, oxygen, carbon dioxide, etc.) and/or may be suitable for use in another application (e.g., cosmetics, beverages, biotech applications, etc.) where microbial testing of the gas is desired.

The gas source is coupled to the microbial test unit through a regulator 504 and at least one valve 506. The at least one valve 506 controls the flow of compressed gas from the gas source 502 to the microbial test system 400. The regulator 504 is configured to regulate the pressure and flow rate of the compressed gas input to the microbial test system 400. In one embodiment, the pressure of the compressed gas input to the microbial test system 400 is from about 20 psi to about 80 psi. In another embodiment, the pressure of the compressed gas input to the microbial test system 400 is from about 40 psi to about 70 psi. In yet another embodiment, the pressure of the compressed gas input to the microbial test system 400 is equal to or greater than about 60 psi.

An orifice (not shown) is present at the outlet of the regulator that controls the flow rate of gas into the microbial test system 400. The orifice may be any suitable shape and size. In one embodiment, the orifice is an annular orifice having a diameter of about 0.050 inch to about 0.1 inch. In another embodiment, the orifice is an annular orifice having a diameter of about 0.060 inch to about 0.080 inch. In yet another embodiment, the orifice is about 0.070 inch. The flow rate of the compressed gas input to the microbial test system 400 is a function of the pressure of the compressed gas and the size of the orifice. For example, in an embodiment where the regulator 504 regulates the compressed gas to about 60 psi and the orifice has a diameter of about 0.070 inch, the flow rate of the compressed gas input to the microbial test system 400 may be about 5 CFM. In other embodiments, the pressure of the compressed gas and/or the size of the orifice may be set to provide a suitable flow rate of the compressed gas into the microbial test system 400. For example, in one embodiment, the pressure of the compressed gas and/or the size of the orifice may be set to provide a flow rate of the compressed gas input to the microbial test system 400 from about 0.5 CFM to about 10 CFM. In another embodiment, the pressure of the compressed gas and/or the size of the orifice may be set to provide a flow rate of the compressed gas input to the microbial test system 400 from about 4 CFM to about 8 CFM. In yet another embodiment, the pressure of the compressed gas and/or the size of the orifice may be set to provide a flow rate of the compressed gas input to the microbial test system 400 equal to or greater than about 5 CFM.

The decompression region 348 and the sampling region 350 define a flow path through the internal cavity 316 of the microbial test unit 300 between the inlet 346 and the outlet 352. In embodiments where the microbial test unit 300 and the sample dish 100, 200 (e.g., including the microbial growth substrate 150) form the microbial test system 400, the flow path may additionally include the radially extending passages formed by the flow channels 368 and the base 102 of the sample dish 100, 200.

The flow of gas through the microbial test system 400, as well as the process for testing a microbial content of a compressed gas will now be described with reference to FIG. 15. As shown, the exemplary microbial test system 400 is provided as the microbial test unit 300 having at least one microbial growth substrate 150 retained by the sample dish 100 contained in the sampling region 350. The flow of air through the microbial test system 400 is discussed herein with references to stages A-E.

At stage A, compressed gas is input to the decompression region 142 of the internal cavity 104 through the inlet.

At stage B, the compressed gas is incident on the surface 338 of the plate 336, and is directed radially outward with respect to the longitudinal axis 322 in the decompression region 348. This radial spreading effectuates decompression of the compressed gas. In some embodiments, the compressed gas may be decompressed to atmospheric or near atmospheric conditions. Decompression of the gas reduces the impaction velocity and stress of the microbial cells onto the microbial growth substrate, thereby improving the microbial recovery.

At stage C, the decompressed gas is incident the first stepped portion 332 of the internal surface 330, and is redirected through the gap 344 into the sampling region 350. The redirection of the gas and the size of the gap 344 through which the decompressed gas passes create turbulent flow of the gas into the sampling region 350. The decompressed gas is therefore brought into contact with the microbial growth substrate 150. The turbulent flow aids in the distribution of decompressed gas incident the microbial growth substrate 150.

At stage D1, a portion of the sampled gas flows through the gap 406 formed between the sample dish 100 and the inner surface 330 (e.g., the second stepped portion 334) of the housing 302. The sampled gas enters the channel inlet 402 and flows through the radially extending passage.

Meanwhile, at stage D2, a portion of the sampled gas flows through the open distal end 358 of the cuff 354 (and the opening of the sample dish). The open distal end 358 of the cuff 354 (and the opening of the sample dish) further aids in the distribution of decompressed gas incident the microbial growth substrate 150 by creating a flow path proximate the center of the sample dish. This flow path encourages the turbulent gas entering the sampling region to be more extensively distributed throughout the sampling region and to come into contact with the microbial growth substrate 150.

At stage E, the sampled gas exits the microbial test system. More specifically, the portion of the sampled gas that enters the open distal end of the cuff 354 flows through the cuff 354 and exits the microbial test system through the outlet 352. The portion of the sampled gas that enters the channel inlet 402 and flows through the radially extending passage exits the passage outlet 404.

The testing process may be conducted for any suitable amount of time. In one embodiment, the time of performing the testing process is from about 15 seconds to about 5 minutes. In another embodiment, the time of performing the testing process is from about 15 seconds to about 1 minute. In another embodiment, the time of performing the testing process is from about 1 minute to about 2 minutes. In another embodiment, the time of performing the testing process is from about 2 minutes to about 3 minutes. Following the testing process, the sample dish 100, 200 including the microbial growth substrate 150 may be removed from the microbial test unit 100 and may be analyzed for the presence of microbes. For example, the microbial growth substrate 150 may be incubated for a suitable time at a suitable temperature to facilitate growth of microbes collected on the microbial growth substrate 150. The microbial growth substrate may subsequently be analyzed for the presence of microbial growth.

The microbial test unit of the present disclosure provides the advantage of providing a test unit to which compressed gas may be directly input. More specifically, the microbial test unit provides the ability to directly test compressed gas and collect bacteria due to positive pressure from the compressed gas pushing the microbes onto the microbial growth substrate. The microbial test unit is portable and does not require a power source. As such, the microbial test unit is particularly applicable as a field test unit, e.g., in a food processing plant environment.

In addition, the microbial test system may provide improved air flow and distribution of the gas on the surface of the microbial growth substrate. This may allow for improved microbial detection as compared with a microbial test system that utilizes a conventional sample dish.

The following example demonstrates the compressed gas sampling capability of the microbial test system 400 of the present disclosure, as compared to the compressed gas sampling capability of a microbial test system that utilizes a conventional sample dish (e.g., a conventional Petri dish that does not include a opening extending through the base or an inner side wall) and includes a microbial test unit that does not include a cuff (e.g., a microbial test unit as described in U.S. Pat. No. 8,753,835).

Referring now to FIG. 16, an experimental bacterial nebulization and sampling system including the microbial test system 400 is schematically shown at 600. The microbial test system 400 is coupled to the gas source 602 through regulators 604, 606, 608, nebulizer 610, desiccant 612, and flow rate meter 614.

The gas source 602 is compressed air suitable for use in the food manufacturing industry. The pressure and flow rate of the compressed air exiting the gas source is regulated by regulator 604. For purposes of the experiment, the pressure of the compressed air was regulated to 60 psi.

The regulators 606 and 608 are coupled in parallel to the regulator 604. A portion of the compressed air exiting the regulator 604 is passed through the regulator 606, and another portion of the compressed air exiting the regulator 606 is passed through the regulator 608. For purposes of the experiment, the pressure of the compressed air passed through the regulator 606 was further regulated to 45 psi, and the pressure of the compressed air passed through the regulator 608 was further regulated to 40 psi.

The nebulizer 610 is coupled to the regulator 606. The compressed air exiting the regulator 606 passes through the nebulizer (at 45 psi) to entrain bacteria in the compressed air. For purposes of the experiment, Gram positive, non-spore forming bacteria *Micrococcus luteus* ATCC 4698 was contained in the nebulizer. This organism is commonly used in testing the recovery of bacteria from aerosols. *Micrococcus luteus* ATCC 4698 has a round to slightly elongated round shape with a diameter between 0.5-1 µm. Cells of this organism after growing in broth can exist as single cells, groups of tetrads or clumps. Broth cultures for each experiment were prepared by inoculating a loopful of working culture into 50 ml tryptic soy broth (TSB) and grown with agitation (200 rpm) for 18 hours at 32° C.

The desiccant 612 is coupled to the nebulizer 610 for removing excess moisture in the system. The desiccant 612 used for purposes of the experiment was DRIERITE gypsum desiccant, available from W. A. Hammond Drierite Co., Xenia Ohio.

The flow rate meter 614 is coupled to the desiccant 612 and the regulator 608. The flow rate meter 614 monitors the flow of the compressed gas to the microbial test system 400. The compressed air exiting the desiccant 612 is rejoined with the compressed air exiting the regulator 608 at 40 psi. In the experimental bacterial nebulization and sampling system 600 shown in FIG. 16, the compressed air is input to the microbial test system 400 at 40 psi.

With continued reference to FIG. 16, a sterile sample dish including agar (tryptic soy agar medium) was placed into the ethanol sanitized microbial test unit 300 so as to form the microbial test system 400. The compressed gas was input to the microbial test system 400 at a flow rate of 1.6 CFM. Three 30 L sampling runs were conducted, each run being conducted by passing 30 L of air through the microbial test system. Three 60 L sampling runs were also conducted, each run being conducted by passing 60 L of air through the microbial test system. After each sampling run (each 30 L sampling run and each 60 L sampling run), the sample dish was removed and the microbial test unit 300 was wiped down with a 70% ethanol solution and a new sample dish was added. In addition, before and after each sampling run (each 30 L sampling run and each 60 L sampling run), the nebulizer was weighed to calculate the approximate volume of liquid nebulized during the sampling run. After each sampling run, the used liquid was removed and replaced with a fresh bacterial solution for the next sampling run.

The sample dishes used in the sampling runs were each incubated at 32° C. for 24 hours. Following the incubation period, colony numbers were determined using an automated plate counting system (Q-count, Spiral Biotech).

With additional reference to FIG. 17, a similar experimental bacterial nebulization and sampling system is schematically shown at 700. The nebulization and sampling system differs from the system 600 in that the microbial test system 616 used for microbial detection is different. The microbial test system 616 is similar to that described in U.S. Pat. No. 8,753,835. Specifically, the microbial test system 616 utilizes a conventional sample dish (e.g., a conventional Petri dish that does not include an opening extending through the base or an inner side wall), and includes a microbial test unit that does not include a cuff.

As shown in the results of the 30 L experiment (Table 1), the microbial test system 400 recovered more than double the number of colony-forming units (CFU) than the microbial test system 616. That is, the number of viable microbes present on the growth media substrate of the microbial test system 400 is higher than the number present on the growth media substrate of the microbial test system 616.

TABLE 1

| 30 L air | | | | |
|---|---|---|---|---|
| | Microbial Test System 616 | | Microbial Test System 400 | |
| | CFU/plate | CFU/L air | CFU/plate | CFU/L air |
| Replicate #1 | 133.00 | 4.43 | 249.00 | 8.30 |
| Replicate #2 | 137.00 | 4.57 | 250.00 | 8.33 |
| Replicate #3 | 80.00 | 2.67 | 297.00 | 9.90 |
| Avg. value | 116.67 | 3.89 | 265.33 | 8.84 |
| St. dev. | 25.98 | 0.87 | 22.40 | 0.75 |

As shown in the results of the 60 L experiment (Table 2), the microbial test system 400 again recovered more than double the number of CFU than the microbial test system 616.

TABLE 2

| | 60 L air | | | |
|---|---|---|---|---|
| | Microbial Test System 616 | | Microbial Test System 400 | |
| | CFU/plate | CFU/L air | CFU/plate | CFU/L air |
| Replicate #1 | 88.00 | 1.47 | 325.00 | 5.42 |
| Replicate #2 | 163.00 | 2.72 | 283.00 | 4.72 |
| Replicate #3 | 179.00 | 2.98 | 275.00 | 4.58 |
| Avg. value | 143.33 | 2.39 | 294.33 | 4.91 |
| St. dev. | 39.67 | 0.66 | 21.93 | 0.37 |

The results of the above experiments demonstrate that the microbial test system 400 may provide comparable or superior microbial detection of microbes present in compressed gas. The results demonstrate that the levels of impact stress on the microbes (i.e., due to impaction velocity of the microbial cells on the agar surface, design parameters of the microbial test unit, and/or operating parameters) does not negatively affect microbial recovery on the agar. Furthermore, results demonstrate that the design of both the sample dish and microbial test unit may allow for improved air flow and distribution of the gas on the surface of the microbial growth substrate. This may allow for improved microbial detection as compared with a microbial test system that utilizes a conventional sample dish.

Although the invention has been shown and described with respect to a certain embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A sample dish, comprising:

a base extending in a direction along a longitudinal axis between opposed first and second surfaces and extending radially outward in a direction orthogonal to the longitudinal axis, the base comprising an outer periphery extending between the opposed first and second surfaces, an opening extending through the base between the opposed first and second surfaces, and an inner periphery extending between the opposed first and second surfaces and defined by the opening;

an outer side wall at the outer periphery of the base, the outer side wall extending from the first surface of the base in a direction along the longitudinal axis;

an inner side wall at the inner periphery of the base, the inner side wall extending from the first surface of the base in a direction along the longitudinal axis; and at least one channel at the second surface of the base, the at least one channel extending between the outer periphery and the inner periphery.

2. The sample dish of claim 1, wherein the opening and inner side wall are concentric with the outer periphery.

3. The sample dish of claim 1, wherein the at least one channel extends from the outer periphery to the inner periphery.

4. The sample dish of claim 3, wherein the at least one channel extends linearly from the outer periphery to the inner periphery.

5. The sample dish of claim 1, wherein the first surface of the base, the outer side wall, and the inner side wall form a receptacle configured to hold a microbial growth substrate.

6. The sample dish of claim 5, further comprising at least one partition wall extending from the first surface of the base in a direction along the longitudinal axis, the at least one partition wall arranged to divide the receptacle into two or more sub-regions.

7. A microbial test unit, comprising:

a housing extending along a longitudinal axis between a first end and a second end, the housing defining an internal cavity configured to contain a sample dish;

an outlet passing through the housing at the second end of the housing;

a cuff extending along the longitudinal axis into the internal cavity from the outlet, the cuff being an open-ended member configured to extend through an opening of the sample dish and provide fluid communication between the internal cavity and the outlet; and a plurality of ribs projecting into the internal cavity along the longitudinal axis, each of the plurality of ribs extending between the cuff and an inner surface of the housing, each of the plurality of ribs configured to mate with a respective channel of the sample dish.

8. The microbial test unit of claim 7, wherein each of the plurality of ribs radially extends from the cuff to the inner surface of the housing.

9. The microbial test unit of claim 8, further comprising a flow channel provided between respective ones of the plurality of ribs, the flow channel radially extending between the cuff and the inner surface of the housing.

10. The microbial test unit of claim 9, wherein the cuff comprises an opening configured to provide fluid communication between the flow channel and the outlet.

11. A microbial test system, comprising:

the microbial test unit of claim 7; and a sample dish, comprising:

a base extending in a direction along the longitudinal axis between opposed first and second surfaces and extending radially outward in a direction orthogonal to the longitudinal axis, the base comprising an outer periphery extending between the opposed first and second surfaces, an opening extending through the base between the opposed first and second surfaces, and an inner periphery extending between the opposed first and second surfaces and defined by the opening;

an outer side wall at the outer periphery of the base, the outer side wall extending from the first surface of the base in a direction along the longitudinal axis; and an inner side wall at the inner periphery of the base, the inner side wall extending from the first surface of the base in a direction along the longitudinal axis.

12. The microbial test system of claim 11, wherein:

the sample dish comprises a plurality of channels at the second surface of the base, each of the channels extending between the outer periphery and the inner periphery, each of the channels configured to mate with a respective one of the plurality of ribs.

13. The microbial test system of claim 12, wherein
the microbial test unit further comprises a flow channel provided between respective ones of the plurality of ribs, the flow channel radially extending between the cuff and the inner surface of the housing;
the second surface of the base collectively forms a passage with the flow channel; and
the cuff comprises an opening configured to provide fluid communication between the passage and the outlet.

14. The microbial test unit of claim 7, wherein:
the internal cavity comprises a decompression region for decompressing compressed gas input to the internal cavity and a sampling region in fluid communication with the decompression region for containing the sample dish, the decompression region and the sampling region defining a flow path through the internal cavity;
an inlet is at the first end of the housing proximate the decompression region;
the outlet is proximate the sampling region; and
the cuff extends along the longitudinal axis into the sampling region from the outlet, the cuff configured to provide fluid communication between the sampling region and the outlet.

15. The microbial test unit of claim 14, wherein each of the plurality of ribs radially extends from the cuff to the inner surface of the housing.

16. The microbial test unit of claim 15, further comprising a flow channel provided between respective ones of the plurality of ribs, the flow channel radially extending between the cuff and the inner surface of the housing.

17. The microbial test unit of claim 16, wherein the cuff comprises an opening configured to provide fluid communication between the flow channel and the outlet.

18. A microbial test system, comprising:
the microbial test unit of claim 14; and
a sample dish, comprising:
a base extending in a direction along the longitudinal axis between opposed first and second surfaces and extending radially outward in a direction orthogonal to the longitudinal axis, the base comprising an outer periphery extending between the opposed first and second surfaces, an opening extending through the base between the opposed first and second surfaces, and an inner periphery extending between the opposed first and second surfaces and defined by the opening;
an outer side wall at the outer periphery of the base, the outer side wall extending from the first surface of the base in a direction along the longitudinal axis; and
an inner side wall at the inner periphery of the base, the inner side wall extending from the first surface of the base in a direction along the longitudinal axis.

19. A microbial test system, comprising:
a microbial test unit, comprising:
a housing extending along a longitudinal axis between a first end and a second end, the housing defining an internal cavity configured to contain a sample dish;
an outlet passing through the housing at the second end of the housing; and
a cuff extending along the longitudinal axis into the internal cavity from the outlet, the cuff being an open-ended member configured to extend through an opening of the sample dish and provide fluid communication between the internal cavity and the outlet; and
a sample dish, comprising:
a base extending in a direction along the longitudinal axis between opposed first and second surfaces and extending radially outward in a direction orthogonal to the longitudinal axis, the base comprising an outer periphery extending between the opposed first and second surfaces, an opening extending through the base between the opposed first and second surfaces, and an inner periphery extending between the opposed first and second surfaces and defined by the opening;
an outer side wall at the outer periphery of the base, the outer side wall extending from the first surface of the base in a direction along the longitudinal axis; and
an inner side wall at the inner periphery of the base, the inner side wall extending from the first surface of the base in a direction along the longitudinal axis.

20. The microbial test system of claim , wherein:
the internal cavity comprises a decompression region for decompressing compressed gas input to the internal cavity and a sampling region in fluid communication with the decompression region for containing the sample dish, the decompression region and the sampling region defining a flow path through the internal cavity;
an inlet is at the first end of the housing proximate the decompression region;
the outlet is proximate the sampling region; and
the cuff extends along the longitudinal axis into the sampling region from the outlet, the cuff configured to provide fluid communication between the sampling region and the outlet.

* * * * *